United States Patent [19]

McLean

[11] Patent Number: 5,496,567
[45] Date of Patent: Mar. 5, 1996

[54] COMPOSITION HAVING BUFFERING AND NUTRITIONAL PROPERTIES

[76] Inventor: Linsey McLean, G-4267 South State Rd., Davison, Mich. 48423

[21] Appl. No.: 112,768

[22] Filed: Aug. 26, 1993

[51] Int. Cl.[6] .................. A61K 33/08; A61K 33/00; A61K 31/315; A61K 31/195

[52] U.S. Cl. .................. 424/692; 424/715; 514/494; 514/561

[58] Field of Search .................. 514/251, 276, 514/345, 52, 356, 494, 561; 424/715, 692

[56] References Cited

U.S. PATENT DOCUMENTS

| | | | |
|---|---|---|---|
| 3,215,601 | 11/1965 | Stolar | 167/55 |
| 3,253,988 | 5/1966 | Scott | 167/55 |
| 3,272,703 | 9/1966 | Rubino et al. | 167/55 |
| 3,843,778 | 10/1974 | Diamond et al. | 424/38 |
| 4,167,564 | 9/1979 | Jensen | 424/177 |
| 4,172,072 | 10/1979 | Ashmead | 260/115 |
| 4,327,076 | 4/1982 | Puglia et al. | 424/38 |
| 4,327,077 | 4/1982 | Puglia et al. | 424/38 |
| 4,396,604 | 8/1983 | Mitra | 424/154 |
| 4,446,135 | 5/1984 | Fountaine | 424/154 |
| 4,486,412 | 12/1984 | Shah et al. | 424/156 |
| 4,533,543 | 8/1985 | Morris et al. | 424/38 |
| 4,545,989 | 10/1985 | Becker et al. | 424/154 |
| 4,581,381 | 4/1986 | Morris et al. | 514/819 |
| 4,605,551 | 8/1986 | Buehler et al. | 424/38 |
| 4,704,269 | 11/1987 | Korab | 424/44 |
| 4,764,574 | 8/1988 | Grimberg | 424/38 |
| 4,867,989 | 9/1989 | Silva et al. | 426/5 |
| 4,888,185 | 12/1989 | Miller | 424/440 |
| 4,937,076 | 6/1990 | Lapidus | 424/441 |

*Primary Examiner*—Raymond Henley, III
*Attorney, Agent, or Firm*—Harness, Dickey & Pierce

[57] ABSTRACT

A liquid pharmaceutical composition having buffering properties comprises as its primary ingredients calcium carbonate ($CaCO_3$) and magnesium oxide (MgO; magnesia) or magnesium hydroxide ($Mg(OH)_2$) that form the base for the compound. The base is carried in a suspension of oil and water. Lecithin ($CH_2(R)CH(R')CH_2OPO(OH))(CH_2)_2N(OH)(CH_2)_3$ is provided as an emulsifier and potassium sorbate ($CH_3CH{:}CHCH{:}CHCOOK$) is provided as a preservative. Other ingredients include vitamin complexes, selected metal chelates as antipathogens, and flavorings.

22 Claims, No Drawings

COMPOSITION HAVING BUFFERING AND NUTRITIONAL PROPERTIES

BACKGROUND OF THE INVENTION

I. Field of the Invention

The present invention relates to compositions of matter having buffering and nutritional properties. More particularly, the present invention relates to a liquid composition that includes a vegetable oil and water suspension that includes therein an antacid base comprising calcium carbonate and magnesium oxide or magnesium hydroxide. The composition further includes selected metal chelates or complexes and a vitamin supplement. The composition of the present invention has both buffering and nutritional properties. The composition may be administered in liquid form or within a capsule or tablet.

II. Description of the Relevant Art

Life in modern times is, by definition, life in stressful times. The well-being of the individual is clearly compromised by the fast-paced, high-stress styles of life that most Westerners have come to expect as being normal and acceptable.

While many parts of the human body suffer from such a way of life, the stomach and the duodenum represent areas of the body that react most immediately and most vividly to increased stress on the individual.

Two undesirable situations result from stress. First, the body tends to absorb and metabolize important nutrients, particularly the B complex vitamins (the most important of which are vitamins $B_1$, $B_2$, $B_6$ and $B_{12}$), at a particularly fast rate. Also metabolized at an accelerated rate are metal elements including calcium, magnesium and zinc.

The second situation relates to the physical destruction of body tissue. In the healthy stomach, gastric mucus and epithelial barrier protect the stomach from "digesting itself". This is critical in that pure gastric juice is capable of digesting all living tissues. Pathogenically, severe and even mild stress works to compromise these lines of defense by causing an alteration in the permeability of the epithelial barrier thereby allowing back diffusion of hydrochloric acid and contributing to the destruction of underlying tissue Histamine is liberated and plays a role in the stimulation of additional acid and pepsin secretion. The mucosa is damaged as a result and erosions and ulcers may be formed. Plasma protein is lost at this stage.

In responding to the former situation, an increased uptake of selected vitamins and metals by the affected individual works to offset the loss due to stress. Regarding the latter situation, the primary objective in the treatment of erosions and ulcers is to inhibit (or buffer) the acid secretions. Such inhibition results in both relieving symptoms and encouraging healing of the affected region.

To this end, antacids are useful for neutralizing the acid gastric contents by maintaining an elevated pH level such that pepsin is not activated. The buffering feature of antacids is generally provided by a weak base that becomes a buffer on the addition of acid.

A typical antacid uses as its principal ingredient magnesium hydroxide ($Mg(OH)_2$), which also finds use as a laxative in milk of magnesia (magnesia magma) in a water suspension. The typical antacid also uses aluminum, typically in the form of aluminum hydroxide gel ($Al_2O_3 xH_2O$). However, aluminum has been related to Alzheimer's disease on the theory that because aluminum is a neurotoxin, it can induce neurofibrillary changes in the brain. This is the result of aluminum toxicity. While it is not clear whether or not the link between the disease and aluminum is absolute, this theory persists.

There are known some antacids that do not contain aluminum, but use other undesirable components. For example, some popular antacids contain "mineral oil and purified water". However, while mineral oil has had for some time been used internally, it is now becoming clear that this is not desirable. Mineral oil taken internally has many negative effects. For example mineral oil decreases absorption of vitamins A, D, E, and K, as well as calcium and phosphorous. Furthermore, mineral oil binds carotene from foods in the intestine as it passes. Mineral oil also passes into blood and into the lymph, and picks up additional fat soluble vitamins from body fluids and tissues and excretes these materials in the feces. In addition, mineral oil, which is often used as a laxative (thus the individual using the composition as an antacid will be receiving treatment with a laxative even if such treatment is unnecessary), is also under present suspicion as a contributor to cancer.

Buffering compositions not containing mineral oil are known. However, the compositions substitute mineral oil with other oils that are not desirable according to present knowledge. Specifically, all of the oils used in known compositions are either saturated or are polyunsaturated. Today it is understood that polyunsaturates contribute to cancer because of low-density lipoproteins ("LDL's") and because of the generation of free radicals. Polyunsaturates depress both the density of the LDL's while reducing the numbers of desirable high density lipoproteins ("HDL's").

Furthermore, only LDL elevation is associated with increased coronary risk, while HDL elevation correlates with decreased risk. Accordingly, HDL cholesterol has been referred to as "benevolent" cholesterol, and HDL elevation is increasingly being thought of as having protective effects.

In any event, stressful conditions lead to both excess acidity and nutrient (particularly vitamin) deprivation. There is presently no known pharmaceutical composition which attends to both of these difficulties as a single medication.

SUMMARY OF THE PRESENT INVENTION

The present invention provides a solution to the problems described above by offering the user both a means of reducing stomach acidity while at the same time providing a nutritional supplement for compromised individuals.

The composition of the present invention includes an antacid base and a liquid carrier in which the base is suspended. The liquid carrier is a combination of an unsaturated vegetable oil and water The composition may be administered in liquid form or may be a liquid encapsulated in a tablet, such as a gelatin capsule. The base comprises calcium carbonate and magnesium oxide or magnesium hydroxide.

Additionally supplied as part of the present invention is an emulsifier (preferably lecithin) and a preservative (such as potassium sorbate).

Additional ingredients are included. First among these is a vitamin supplement comprising selected vitamins. In addition a variety of metal chelates provides nutritional support and healing of the body. The preferred chelates include chelates of trace minerals and calcium amino acid chelates, magnesium amino acid chelates, and zinc amino acid chelates.

In addition secondary ingredients may be added in the form of flavorings and sweeteners as needed.

The principal advantage of the present invention is that the user can obtain both relief from excess acidity and nutrition from the same medication without the fear of aluminum toxicity. These two actions combined produce in the user a considerable sense of well-being for three reasons. First, the user's abdominal discomfort is diminished. Second, the effects of the selected vitamins (particularly B vitamins) work to provide additional calm. Third, the healing effect of the metal chelates improves the general health of the affected individual. The overall sense in the user is that stress is reduced emotionally as well as physically as a result of the effects of the present invention.

Other objects and details of the present invention will become apparent from the following detailed description.

DETAILED DESCRIPTION OF THE PREFERRED EMBODIMENTS OF THE PRESENT INVENTION

The composition of the present invention includes as its basic components a base and a liquid in which the base is suspended.

The antacid base comprises two primary ingredients. These ingredients include calcium carbonate ($CaCO_3$), and magnesium oxide (magnesia) (MgO) or magnesium hydroxide ($Mg(OH)_2$).

Calcium carbonate is slightly soluble in water and is soluble in acids. It is provided as a component of the present invention to act as a neutralizing antacid. Because it is provided in a liquid suspension in the present invention, its nuisance particulate character is eliminated.

Magnesium oxide, like calcium carbonate, is slightly soluble in water and is soluble in acids. It is often used in pharmaceutical compositions. Magnesium hydroxide is somewhat soluble in water and is soluble in solutions of ammonium salts and dilute acids. Magnesium helps to buffer acids at the cellular level.

According to the present invention the two primary components of the base, calcium carbonate and magnesium oxide or magnesium hydroxide function not only as buffering antacids but also as calcium and magnesium supplements. Both are essential substituents of living things. They are also known to relieve stress.

The present composition also comprises a liquid carrier that acts as a suspension for the base materials. The suspension is comprised of a mixture of water and an oil (preferably canola oil) which is partially soluble in water.

Canola oil is a vegetable oil derived from the seeds of the cabbage-like canola plant, *Brassica campestris*. The oil derivative is high in unsaturated fats and acids, including erucic, linolenic and linoleic acids. The oil has a high content of apolipo proteins made up of single, hydrophobic 19-k polypeptides. Like rapeseed oil from the very similar rapeseed plant, it is an edible oil that may be substituted for soybean oil. Canola oil has value for use in low-fat diets.

Olive oil may be used as an alternative to canola oil in the water and oil suspension. While not necessarily the preferred oil, olive oil is considered a suitable substitute for canola oil. Olive oil is a nondrying oil that is sparingly soluble in alcohol It comprises as its chief constituents oleic acid, palmitic acid, and linoleic acid.

The oils used in the present invention are known to balance moods by enhancing the operations of neurotransmitters in the brain.

Canola oil (as well as olive oil) is high in monounsaturates. These unsaturates compare favorably with polyunsaturates. As noted, some antacids have previously used polyunsaturates, and these unsaturates are not desirable because of their tendency to reduce the density of LDL's as well as the number of HDL's. Conversely, monounsaturates have been found to lower cholesterol by reducing the numbers of LDL's while maintaining and often elevating the number of HDL's.

The addition of the oil provides a fatty substituent that is useful in delaying the passage of the present composition out of the stomach. The process thus slowed, the composition provides a "time release" effect.

In addition to the base and liquid carriers, an emulsifier is preferably included in the composition as a surface-active agent. The emulsifier of choice is lecithin $(CH_2(R)CH(R')CH_2OPO(OH)O(CH_2)_2N(OH)(CH_2)_3)$, although other emulsifiers may be used In its pure form, lecithin is a phosphatidyl choline derived from seeds or animal sources.

Additional ingredients of the composition of the present invention include a preservative such as potassium sorbate ($CH_3CH{:}CHCH{:}CHCOOK$) (other preservatives may be used), sweeteners, and flavorings as needed.

Beyond the basic ingredients given above, a variety of additional ingredients may be included in the pharmaceutical composition according to the present invention. The additional ingredients include vitamin supplements and selected chelates.

A variety of selected vitamins may be used. The vitamin supplements are preferably those that are directed to the overall reduction of stress of the user, this in keeping with one of the main purposes of the invention. Accordingly, the vitamin B complex may be selected. This group preferably includes thiamine ($B_1$) (available as thiamine hydrochloride and thiamine mononitrate), riboflavin ($B_2$), different chemical forms of what is now considered to be $B_3$, different chemical forms of what is now considered to be $B_5$, pyridoxine HCl ($B_6$) and cyanocobalamin ($B_{12}$). These additives are used, when compatible with the other components, as microencapsulates. When used in this form, the microencapsulates are used to provide the composition in a tablet form. Additionally, the composition may be provided in a chewable form with, for example, a fruit flavor.

Other vitamins may be selected. For example, the antineuritic vitamin thiamine has particular application in reducing emotional hypersensitivity, muscular weakness and fatigue. Riboflavin is important in tissue respiration. Pyridoxine is essential for the dehydration and desulfydration of amino acids and for the normal metabolism of tryptophan. It also appears to be related to fat metabolism. Inadequate amounts of $B_{12}$ in humans results in deficiencies that include megaloblastic anemias and various neurologic disorders.

Metal chelates are often found in biological systems. For example, they represent the iron-binding group of hemoglobin. Metal chelates are also known to be effective against gram-positive bacteria, fungi and viruses. Amino acid chelates are known to aid in healing processes.

The composition of the present invention includes as additional ingredients selected metal chelates such as calcium, magnesium or zinc amino acid chelates. (Zinc oxide may be used in lieu of or in addition to the zinc amino acid chelate. In either form, zinc enhances the body's immune system and this enhancement is believed to be beneficial against various pathogens including, it is further believed, those bacteria commonly associated with the formation of ulcers). In addition to assisting in the healing of the body, these amino acid chelates also provide supplementary amounts of calcium, magnesium and zinc, all necessary metals to maintain body health and metabolism. Furthermore, the metal chelates promote easier and more complete absorption of nutrients by the body while not changing the pH of the digestive tract which is a common reaction to inorganic salts.

The composition may be provided either as a liquid or as a liquid encapsulated within a tablet or a capsule such as a gelatin capsule.

The ingredients that comprise the composition described above are used as needed in the present composition to provide a liquid pharmaceutical composition having buffering properties.

GENERAL FORMULATION AND PREPARATION OF THE PRESENT COMPOSITION

The composition of the present invention is prepared generally as follows.

The first phase is created when the preferred emulsifier, in the present case lecithin, is dissolved together with the preservative in warm water. It is not necessary that the water be hot. It need only be so warm as to support dissolution of the emulsifier and the preservative. The amount of lecithin added depends on the flavors or sweeteners used. Generally this is between 1–20% of the total weight of the composition. This is generally regarded as a safe level.

Once the emulsifier and the preservative are fully dissolved in the water to create the first phase, the solution is allowed to cool substantially to room temperature.

To the first phase is added the antacid bases. The bases, a calcium carbonate and magnesium oxide or magnesium hydroxide mixture U.S.P., are added at 5:4 ratios by weight. The antacid bases are either in pure form or are microencapsulated, depending upon flavoring requirements. The first phase and the bases are mixed to create a second phase. The oil component is finally added to the second phase to create the product.

Several optional ingredients may be added to the composition and, if added, are included at the creation of the second phase and prior to its being mixed. The optional ingredients include flavorings and sweeteners. Furthermore, and when compatible, B-complex vitamins, other vitamins and mineral supplements may be included as microencapsulates. Finally, metal chelates of trace minerals, calcium, and magnesium may be added as additional nutrients.

The recommended quantities of the components necessary for preparing a minimum workable amount of the present composition are as follows:

| | |
|---|---|
| Water: | 1–55% by weight |
| Emulsifier (lecithin): | 1–10% by weight |
| Antacid base (Calcium carbonate/ Magnesium oxide/hydroxide at 5:4 ratio): | 3–10% by weight |
| Oil: | 10–40% by weight |
| Preservative: | per recommendation of manufacturer |
| Flavorings and Sweeteners: | per recommendation of manufacturer |
| Vitamin Supplement: | 1–5% by weight |
| Mineral Supplements: | 1–10% by weight |
| Amino acid chelates: | 1–10% by weight |

Many of these quantities may be varied based upon continued experimentation and improvements in concentrations of certain components.

EXAMPLE

Approximately 236.5 ml of water was warmed to about 60 degrees Celsius. Thereafter, a quantity of 15 g of lecithin and 1.2 g of potassium sorbate and sodium propionate (as preservatives) was added to the warmed water. These components created the first phase which was thereafter allowed to cool to room temperature.

To the cooled first phase was added 18 g of the antacid base. The base comprised a calcium carbonate-magnesium oxide mixture U.S.P. at a 5:4 ratio by weight. The combination of the first phase and the oil were mixed for approximately 10 minutes at moderate speed. This combination created the second phase.

Supplemental materials were added to the second phase prior to mixing. These materials included vitamins (B-complex and others) in the amount of 3–10 g and minerals (calcium and magnesium) in the amount of 3–5 g. Amino acid chelates of trace minerals were also added to this phase in the amount of 2–3 g.

To the mixed second phase was added 118.3 ml of canola oil. A buffering and nutritional composition of 225 ml was obtained.

I claim:

1. An orally administrable buffering composition in a liquid suspension form for use in a living system comprising:

between 3 and 10 percent by weight of a base, said base comprising a buffering ingredient that is substantially insoluble in a neutral medium;

a liquid suspension, said suspension comprising an oil, said oil being provided in the amount of between 10 and 40 percent by weight, said oil being slightly soluble in water; and between 1 and 5 percent by weight of a vitamin supplement, whereby the buffering composition raises the pH of the living system to which it is administered.

2. The buffering composition of claim 1 wherein said vitamin supplement comprises B complex vitamins.

3. The buffering composition of claim 1 wherein said suspension further includes water, the component of water being provided in the amount of between 1 to 55 percent by weight.

4. The buffering composition of claim 1 wherein said oil is canola oil.

5. The buffering composition of claim 1 wherein said oil is olive oil.

6. The buffering composition of claim 1 wherein said base comprises calcium carbonate and magnesium oxide.

7. The buffering composition of claim 6 wherein said oil is canola oil.

8. The buffering composition of claim 7 wherein said oil is olive oil.

9. The buffering composition of claim 7 wherein said suspension further includes water, the component of water being provided in the amount of between 1 to 55 percent by weight.

10. The buffering composition of claim 7 further comprising an emulsifier, said emulsifier being provided in an amount of between 1 to 10 percent by weight.

11. The buffering composition of claim 10 wherein said emulsifier is lecithin.

12. The buffering composition of claim 10 further comprising a preservative.

13. The buffering composition of claim 12 wherein said preservative is potassium sorbate.

14. The buffering composition of claim 4 further comprising a metal chelate.

15. The buffering composition of claim 2 further comprising trace amounts of a metal chelate.

16. The buffering composition of claim 15 wherein said chelate is selected from the group consisting of calcium amino acid chelates, magnesium amino acid chelates, and zinc amino acid chelates.

17. The buffering composition of claim 1 further including a flavoring.

18. The buffering composition of claim 1 further including zinc oxide.

19. An orally administrable buffering composition in liquid form for use in a living system comprising:
- a base, said base including a buffering ingredient that is substantially insoluble in a neutral medium;
- an emulsifier;
- a preservative;
- a liquid, whereby said base, emulsifier and said preservative are suspended in said liquid; and
- a metal chelate, whereby the buffering composition raises the pH of the living system to which it is administered.

20. An orally administrable buffering composition for use in a living system comprising:
- a base, said base including a buffering ingredient that is substantially insoluble in a neutral medium;
- an emulsifier;
- a preservative; and
- a metal chelate, whereby the buffering composition raises the pH of the living system to which it is administered.

21. An orally administrable buffering composition for use in a living system comprising:
- a base, said base including a buffering ingredient that is substantially insoluble in a neutral medium;
- an emulsifier;
- a vitamin;
- a preservative; and
- a metal chelate, whereby the buffering composition raises the pH of the living system to which it is administered.

22. An orally administrable buffering composition for use in a living system comprising:
- a base, said base including a buffering ingredient that is substantially insoluble in a neutral medium;
- an oil;
- a selected amount of water;
- an emulsifier;
- a preservative; and
- a metal chelate, whereby the buffering composition raises the pH of the living system to which it is administered.

* * * * *

UNITED STATES PATENT AND TRADEMARK OFFICE
CERTIFICATE OF CORRECTION

PATENT NO. : 5,496,567
DATED : March 5, 1996
INVENTOR(S) : Linsey McLean

It is certified that error appears in the above-indentified patent and that said Letters Patent is hereby corrected as shown below:

Column 1, line 42, missing comma after "barrier".

Column 1, line 43, missing period after "tissue".

Column 2, line 8, "had" should be deleted.

Column 2, line 11, missing comma after "example".

Column 2, line 52, missing period after "water".

Column 2, line 62, missing comma after "addition".

Column 3, line 1, missing comma after "addition".

Column 3, line 40, missing comma after "invention".

Column 3, line 42, missing comma after "hydroxide".

UNITED STATES PATENT AND TRADEMARK OFFICE
CERTIFICATE OF CORRECTION

PATENT NO. : 5,496,567
DATED : March 5, 1996
INVENTOR(S) : Linsey McLean

It is certified that error appears in the above-indentified patent and that said Letters Patent is hereby corrected as shown below:

Column 3, line 62, missing period after "alcohol".

Column 4, line 18, missing period after "used".

Column 4, line 24, missing "and" before "sweeteners".

Column 5, line 6, missing comma after "body".

Signed and Sealed this

Sixteenth Day of July, 1996

Attest:

BRUCE LEHMAN

Attesting Officer

Commissioner of Patents and Trademarks